(12) United States Patent
Li et al.

(10) Patent No.: US 11,543,351 B2
(45) Date of Patent: Jan. 3, 2023

(54) ALL-IN-ONE HANDHELD MACHINE FOR TESTING DRUGS IN HAIRS

(71) Applicants: Beijing Zhong-Tianfeng Security Protection Technologies Co., Ltd., Beijing (CN); First Research Institute of The Ministry of Public Security of PRC, Beijing (CN)

(72) Inventors: Bin Li, Beijing (CN); Qing Wang, Beijing (CN); Jun Han, Beijing (CN); Chuan Jin, Beijing (CN); Minnan Zhang, Beijing (CN)

(73) Assignees: Beijing Zhong-Tianfeng Security Protection Technologies Co., Ltd., Beijing (CN); First Research Institute of The Ministry of Public Security of PRC, Beijing (CN)

( * ) Notice: Subject to any disclaimer, the term of this patent is extended or adjusted under 35 U.S.C. 154(b) by 420 days.

(21) Appl. No.: 16/913,018

(22) Filed: Jun. 26, 2020

(65) Prior Publication Data
US 2021/0025822 A1    Jan. 28, 2021

(30) Foreign Application Priority Data
Jul. 22, 2019  (CN) .......................... 201910661214.6

(51) Int. Cl.
| | |
|---|---|
| *G01N 21/64* | (2006.01) |
| *B41J 3/36* | (2006.01) |
| *G01N 33/94* | (2006.01) |
| *G06F 3/041* | (2006.01) |
| *G06Q 50/26* | (2012.01) |

(52) U.S. Cl.
CPC ............ *G01N 21/6428* (2013.01); *B41J 3/36* (2013.01); *G01N 21/645* (2013.01); *G01N 33/94* (2013.01); *G06F 3/041* (2013.01); *G06Q 50/26* (2013.01)

(58) Field of Classification Search
CPC .. G01N 21/6428; G01N 33/94; G01N 21/645; B41J 3/36; G06F 3/041; G06Q 50/26
See application file for complete search history.

(56) References Cited

FOREIGN PATENT DOCUMENTS

CN        206990455 U    *    7/2017

* cited by examiner

*Primary Examiner* — Jennifer Wecker
*Assistant Examiner* — Ali Husain Faraz
(74) *Attorney, Agent, or Firm* — Dicke, Billig & Czaja, PLLC

(57) ABSTRACT

An all-in-one handheld machine for testing drugs in hairs comprises a handheld shell, a control mechanism, a fluorescent immune reagent card test mechanism, an identity recognition mechanism, and a control instruction input unit communicatively connected to the control mechanism are provided in the shell; a shell surface is provided with a reagent card inlet that corresponds to a reagent card socket of the test mechanism; the control mechanism is controllably connected to the test mechanism and the identity recognition mechanism, and is communicatively connected with a communication unit; the control mechanism, the test mechanism and the identity recognition mechanism are all electrically connected to a power supply module. The invention can achieve the functions of identity card reading and wireless data transmission, and the test for trace drug residues in hairs, thereby meeting the requirements for rapidity, portability and accuracy of an on-site test.

20 Claims, 2 Drawing Sheets

ALL-IN-ONE HANDHELD MACHINE FOR TESTING DRUGS IN HAIRS

CROSS-REFERENCE TO RELATED APPLICATIONS

This application is based upon and claims priority to Chinese Patent Application No. 201910661214.6, entitled "All-in-one Handheld Machine for Testing Drugs in Hairs" filed with the China National Intellectual Property Administration on Jul. 22, 2019, which is incorporated herein by reference in its entirety.

TECHNICAL FIELD

The invention relates to the technical field of drug test, in particular to an all-in-one handheld machine for testing drugs in hairs.

BACKGROUND

Urine and saliva tests are a common drug test method at the present stage, which are strictly limited by factors such as the coordination degree of suspicious people and sample extraction environment, and thus have low test work efficiency. In general, urine adulterating and gargling in advance by the tested people, substantially metabolizing and discharging drugs in the urine and the saliva after 24-72 hours of drug use of the tested people and so on will lead to a negative result, causing drug users to escape from legal sanctions and patients abstained from drugs to be out of supervision, and other problems. More importantly, urine metabolites and oral saliva residues of some commonly used legal medicines can interfere with drug testing results from urine and saliva to cause false positives, bring inconvenience to law enforcement. Colloidal gold lateral immunochromatography is the main technical means for a drug test at this stage. However, there are some problems such as low sensitivity, poor reproducibility and so on when using immune colloidal gold test paper for testing, which is only suitable for the urine and saliva test for drug users.

Compared with saliva and urine, hair, as a kind of special biological material for testing, has unique advantages of stable sample properties, easy acquisition, easy preservation, long detection time limit, reflection of the use of drugs for a long time (months or even years) and so on, which overcomes the problems in a traditional drug test by the urine and saliva of sampling inconvenience, short detection time limit, easy interference to testing results by legal drugs and the like. It has broad application prospects in public security first-line combats, such as drug prohibition, criminal investigation, public order and transportation.

However, since the level of drug metabolites in hair is very low, typically only 0.2 ng/mg (2 ng/ml), it has not been used in the field test for drug users due to the lack of rapid and sensitive test techniques over a considerable period of time.

The current main hair drug test methods mainly include:
1) Enzyme-linked immunosorbent assay (ELISA): the method is performed by a complete set of equipment such as an enzyme-labeled instrument, a plate washer, an incubation box and the like, has complicated operation steps, multiple equipment requirements, and high site requirements; and the laboratory test equipment cannot be carried around, the test takes a long time for 45-150 minutes, and the sensitivity is 0.1 ng/mg. In the method, it is required to specially construct a laboratory in a house, and to provide professional technicians in the field of drug test, which can be hardly borne by the district (county and city) finance.

2) Colloidal gold method: in addition to the instrument, it is also necessary to equip a hair breaker. It has low personnel requirements, common personnel can be simply trained for performing the method, the detection time is 5-10 minutes, and the sensitivity is 5 ng/mg. The method usually needs to be used together with the hair breaker, with poor reproducibility, i.e., the testing results for the same sample are often inconsistent at repeated times.

3) Time-resolved fluorescence immunochromatography: it generally adopts a small/handheld instrument. It has low personnel requirements, common personnel can be simply trained for performing the method; and the detection time is about 5 minutes, and the sensitivity is 0.1 ng/mg. However, insufficient and non-uniform fluorescence reaction and poor reagent reproducibility due to the large size of the time-resolved fluorescent microsphere particles, often lead to false positive results.

4) Gas Chromatography-Mass Spectrometry GC/MS: medium and large instruments are required in the method; it has extremely high professional requirements to personnel, and the automatic test cannot be performed; and it has long detection time for 2-4 hours, and a sensitivity of 0.5 ng/mg. The instrument and equipment are expensive; and it has high requirements to environment, personnel and other experimental conditions, and needs long time and high cost for a single test.

Further, the drug abusers can be easily changed into drug traffickers, and the drug taking supported by drug trafficking increases the mobility of the drug abusers and the variability of the organization structure of drug trafficking groups, so that in the inspection process, accurate recognition of the identity of a drug-taking suspect and effective integration of scattered assault test data are the most effective means for restraining the aggravated diffusion of drugs and accurately striking criminal gangs; however, the instrument at the present stage can only perform a single-point test; and the test data results are scattered for each time, the suspect information cannot be accurately identified, and the automatic data uploading function cannot be realized, so that the data has a low effective utilization rate, and finally the dynamic monitoring for drug users cannot be achieved.

SUMMARY

For the defects of the prior art, the invention is directed to provide an all-in-one handheld machine for testing drugs in hairs, which can realize functions of identifying and reading an identity card and wireless data transmission, achieve a test for trace drug residues in hairs, meet the high-sensitivity test requirements of rapidity, portability and accuracy for an on-site test, and directly transmit testing results to a special network by wireless transmission, so that the drug users can be dynamically monitored, the safety of sensitive information of drug users is ensured, and the invention provides a real, accurate and timely data source for constructing big data of drug prohibition.

In order to achieve the above object, the invention adopts the following technical solution.

An all-in-one handheld machine for testing drugs in hairs comprises a handheld shell, wherein a control mechanism, a fluorescent immune reagent card test mechanism, an identity recognition mechanism, a control instruction input unit and a power supply module are provided in the handheld shell; a surface of the handheld shell is provided with a reagent card inlet which just corresponds to a reagent card socket of the fluorescent immune reagent card test mechanism; the control mechanism is controllably connected to the fluorescent immune reagent card test mechanism, the identity recognition mechanism and the control instruction input unit, respectively; the control mechanism, the fluorescent immune reagent card test mechanism, the identity recognition mechanism and the control instruction input unit are all electrically connected to the power supply module; and the control mechanism is communicatively connected with a communication unit comprising a wireless communication module.

Further, the identity recognition mechanism comprises an identity card reading unit, and the control mechanism is controllably connected to the identity card reading unit.

Furthermore, a card reading area is provided at a position, corresponding to the identity card reading unit, on the surface of the handheld shell.

Further, the all-in-one handheld machine for testing drugs in hairs further comprises a printing mechanism, and the control mechanism is controllably connected to the printing mechanism, and the printing mechanism is electrically connected to the power supply module.

Furthermore, the printing mechanism comprises a printing module and a printing paper channel, the control mechanism is controllably connected to the printing module, and the printing module is electrically connected to the power supply module; and a paper outlet for outputting printing papers is provided at a corresponding position of the handheld shell.

Still further, a turnover plate is provided at a position, corresponding to the printing paper channel, at a front surface of the handheld shell, one side of the turnover plate is hinged to the front surface of the handheld shell, and a stop rod for pressing paper is provided at a bottom of the turnover plate; and a locking mechanism is provided between the turnover plate and the front surface of the handheld shell.

Still further, the locking mechanism comprises a ratchet wheel sleeved at one end of the stop rod, a ratchet wheel groove is provided at a position, corresponding to the ratchet wheel, on the front surface of the handheld shell, a pawl is hinged at one end of the turnover plate, and the ratchet wheel and the pawl correspond in position and are matched with each other.

Further, the control instruction input unit is a touch display screen embedded in the front surface of the handheld shell.

The invention also provides a method for utilizing the all-in-one handheld machine for testing drugs in hairs, which comprises the steps of:

S1, after being power-on, inputting a control instruction via the control instruction input unit, and controlling the identity recognition mechanism and the fluorescent immune reagent card test mechanism to start by the control mechanism according to the control instruction;

S2, placing an identity card of a drug-taking suspect on the handheld shell, automatically sensing and reading identity information of the drug-taking suspect from the identify card by the identity recognition mechanism in real time, and transmitting the identity information to the control mechanism;

S3, determining an item to be tested and retrieving a corresponding reagent card, inserting the reagent card with a hair sample collected from the drug-taking suspect into a reagent card socket of the fluorescent immune reagent card test mechanism via the reagent card inlet, selecting by the control instruction input unit a specific test item to be tested, and starting the test by the fluorescent immune reagent card test mechanism after the selection;

S4, automatically operating the fluorescent immune reagent test card mechanism to complete reagent card incubation, detect a fluorescent signal, convert the fluorescent signal into a concentration result for the test item, and transmit the concentration result for the test item to the control mechanism; and S5, transmitting by the control mechanism data of the identity information and the concentration result for the test item of the drug-taking suspect as data to a public security intranet in real time via a wireless communication module; connecting the data into a network base station and uploading the same to a data center platform by the network base station; and issuing the data by the data center platform via the public security intranet to each monitoring point at which a dynamic monitoring on the drug-taking suspect is realized.

Further, the method also comprises controlling by the control mechanism the printing mechanism to print the identity information and the concentration result for the test item of the drug-taking suspect.

The invention has the following beneficial effects.

The all-in-one test machine provided by the invention can be applied to an on-site test for drug abusers at a drug prohibition frontline, and community drug treatment and rehabilitation management and control for drug abusers. It can also be used for drug addiction screening from special crowds such as applicants to be drafted into the Army, civil aviation drivers, civil servants, practitioners in entertainment venues, bus and taxi drivers and the like.

According to the all-in-one test machine of the invention, the identity recognition mechanism is arranged to carry out identity recognition and entry on an owner of a sample to be detected; the control mechanism and the fluorescent immune reagent card test mechanism are arranged so that the control mechanism controls the operation of the fluorescent immune reagent card test mechanism and the identity recognition mechanism; the battery pack supplies power to the control circuit, the fluorescent immune reagent card test machine, the identity recognition mechanism, the printing mechanism and the like; the test data can be temporarily stored in the control mechanism and also be uploaded in real time; and the all-in-one test machine of the invention can be matched with a drug (such as morphine, ice, ketamine, cocaine, fentanyl, etc.) quantum dot fluorescence detection kit for hairs, so that trace drug residues in hair is tested. The all-in-one test machine of the invention can achieve the testing of trace drug residues in hairs, meet the high-sensitivity test requirements of rapidity, portability and accuracy for an on-site test, and directly transmit testing results to a special network by wireless transmission, so that the drug users can be dynamically monitored, the safety of sensitive information of drug users is ensured, and the all-in-one test machine of the invention provides a real, accurate and timely data source for constructing big data of drug prohibition.

DETAILED DESCRIPTION

Hereinafter, the present invention will be further described with reference to the accompanying drawings, in which it should be noted that the present embodiment provides a detailed embodiment and a specific operation process on the basis of the present technical solution, but the scope of the present invention is not limited to the present embodiment.

Embodiment 1

Figure 1:
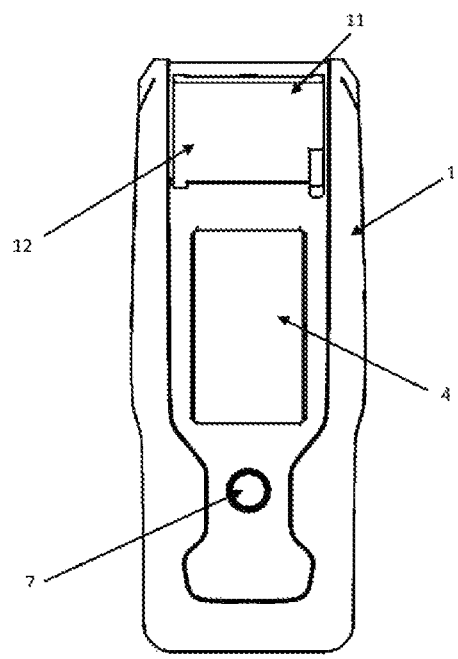
FIG. 1 is a schematic view showing an external structure of an all-in-one machine according to Embodiment 1 of the present invention.
Figure 2:
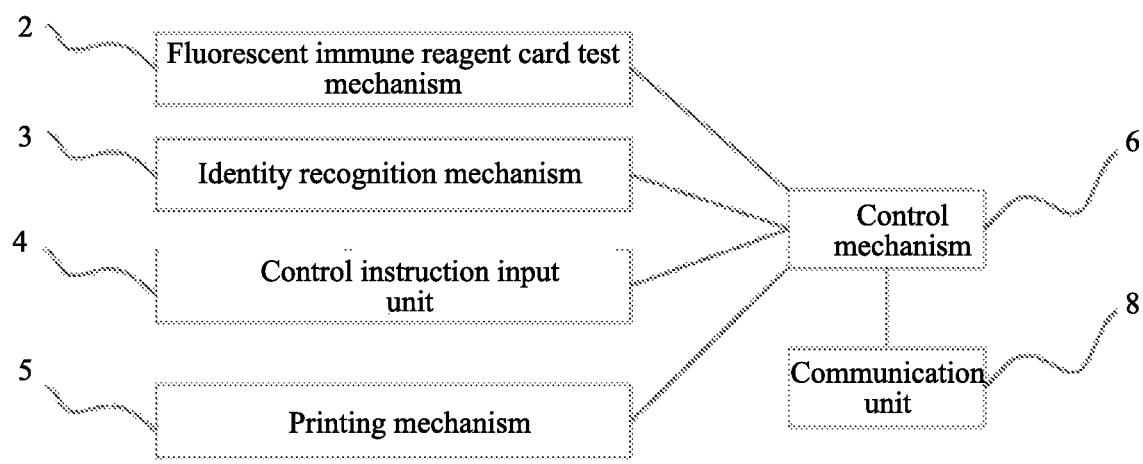
FIG. 2 is a schematic view showing connection of main electric components of the all-in-one machine according to Embodiment 1 of the present invention.
Figure 3:
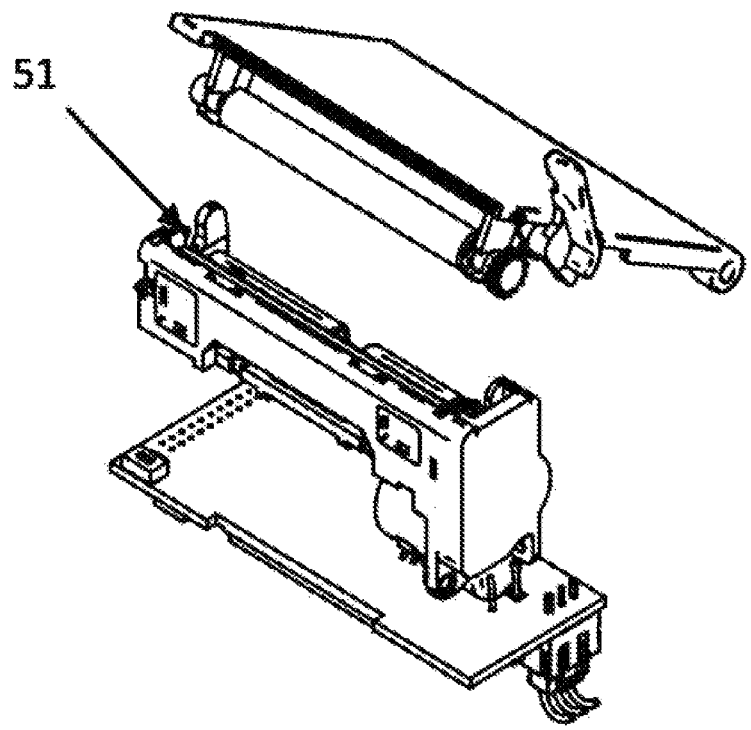
FIG. 3 is a schematic view showing the structure of a printing mechanism of the all-in-one machine according to Embodiment 1 of the present invention.
Figure 4:
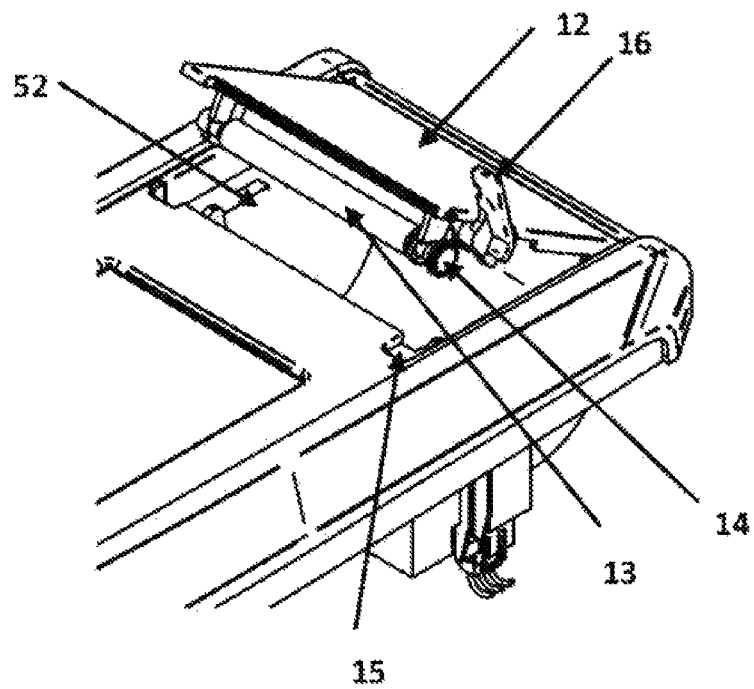
FIG. 4 is a schematic view showing the structure of a turnover plate position on a handheld shell according to Embodiment 1 of the present invention.

The embodiment provides an all-in-one handheld machine for testing drugs in hairs, as shown in FIGS. 1-4, comprising a handheld shell 1, wherein a control mechanism 6, a fluorescent immune reagent card test mechanism 2, an identity recognition mechanism 3, a control instruction input unit 4 and a power supply module are provided in the handheld shell 1; a surface of the handheld shell 1 is provided with a reagent card inlet that corresponds to a reagent card socket of the fluorescent immune reagent card test mechanism 2; the control mechanism 6 is controllably connected to the fluorescent immune reagent card test mechanism 2, the identity recognition mechanism 3 and the control instruction input unit 4, respectively; and the control mechanism 6, the fluorescent immune reagent card test mechanism 2, the identity recognition mechanism 3 and the control instruction input unit 4 are all electrically connected to the power supply module.

Further, in the embodiment, the identity recognition mechanism 3 comprises an identity card reading unit, and the control mechanism 6 is controllably connected to the identity card reading unit.

Furthermore, a card reading area is provided at a position, corresponding to the identity card reading unit, on the surface of the handheld shell 1.

Further, in the embodiment, the handheld shell 1 further comprises a printing mechanism 5, and the control mechanism 6 is controllably connected to the printing mechanism 5, and the printing mechanism 5 is electrically connected to the power supply module.

In the embodiment, the printing mechanism 5 comprises a printing module 51 and a printing paper channel 52, the control mechanism 6 is controllably connected to the printing module 51, and the printing module 51 is electrically connected to the power supply module; and a paper outlet for outputting printing papers 11 is provided at a corresponding position of the handheld shell 1.

Still further, a turnover plate 12 is provided at a position, corresponding to the printing paper channel 52, at a front surface of the handheld shell, one side of the turnover plate 12 is hinged to the surface of the front handheld shell 1, and a stop rod 13 for pressing paper is provided at a bottom of the turnover plate 12; and a locking mechanism is provided between the turnover plate 12 and the front surface of the handheld shell 1.

Still further, the locking mechanism comprises a ratchet wheel 14 sleeved at one end of the stop rod 13, a ratchet wheel groove 15 is provided at a position, corresponding to the ratchet wheel 14, on the front surface of the handheld shell 1, a pawl 16 is hinged at one end of the turnover plate 12, and the ratchet wheel 14 and the pawl 16 correspond in position and are matched with each other.

Further, in the embodiment, the control instruction input unit 4 is a touch display screen embedded in the front surface (middle part) of the handheld shell 1, and the touch display screen is communicatively connected to the control mechanism 6.

Further, in the embodiment, the surface of the handheld shell 1 is provided with a button 7 which is communicatively connected to the control mechanism 6.

Further, in the embodiment, the control mechanism 6 is communicatively connected with a communication unit 8 comprising at least one of a SIM card and a Bluetooth card, the SIM card and/or Bluetooth card are/is disposed within the handheld shell 1.

Further, the communication unit 1 also comprises a USB interface and an SD card socket, wherein the USB interface and the SD card socket are provided on the surface of the handheld shell 1.

More specifically, the handheld shell may comprise a lower shell casing and a cover surface; a hollow space is formed between the lower shell casing and the cover surface; and the control mechanism, the printing mechanism, the fluorescent immune reagent card test mechanism, and a portion of the identity recognition mechanism other than the card reading area are provided in the hollow space. The handheld shell may protect the various components.

The side part of the shell can be formed into a concave curve structure, so that the shell is convenient to be held; and can be added with an antislip strip to improve the holding comfort.

The fluorescent immune reagent card test mechanism 2 can be purchased and arranged according to requirements, such as FIC-H1 series of Hemai technology, which can be matched with a quantum dot fluorescence detection kit for detecting drugs (such as morphine, ice, ketamine, cocaine, fentanyl, etc.) in hairs, so that the test for trace drug residues in hair is realized; different drugs can be tested by the same fluorescence wave band, without the need of frequent switch.

In the embodiment, the reagent card inlet is provided at the surface of the lower shell casing and just corresponds to the reagent card socket of the fluorescent immune reagent card test mechanism.

In particular, the power supply module is a battery pack, and more particularly, a rechargeable battery pack can be used to ensure that the all-in-one test machine of the invention can be operated for more than 10 hours after being charged for once.

In the embodiment, the parameters of the battery pack are 10.8V/3300 mAh/35.64 Wh; however, in actual operations, a person skilled in the art would be able to select a suitable battery pack according to actual requirements.

In the embodiment, the control mechanism 6 mainly comprises a control chip, which may include Cortex A7 series or the like.

In the embodiment, the identity recognition data and the test data can be temporarily stored in the memory of the control chip, and can be uploaded in real time when the SIM card and/or the Bluetooth card are provided.

Specifically, an existing identity card reading unit can be directly adopted as the identity recognition mechanism 3; an RFID chip is contained in the existing second-generation identity card, and information including a name, an address, a photo and the like stored in the RFID chip of the identity card can be obtained via the identity card reading unit. The identity card reading unit can be substantially provided at any position in the handheld shell; and due to the limited volume of the handheld shell, the identity card reading unit can read information stored in the identity card when the identity card is generally placed on the surface of the handheld shell.

In the invention, in order to ensure the card reading effect and more definite indication during use, a card reading area, generally a U-shaped groove, is further provided on the handheld shell. In order to ensure that the card reading is smooth to the maximum extent, the bottom surface of the card reading area can be parallel to the end surface of the lower shell casing, so that the identity card can be as close to the card reading area as possible.

In the embodiment, the printing mechanism may employ thermal printing techniques, and is primarily used for collating suspect information and testing results to print reports.

In the embodiment, the turnover plate is specifically provided on the cover surface; due to the fact that the fluorescent immune reagent card test mechanism is provided, the whole all-in-one machine should be kept stable to reduce sharp operations such as waggling, shaking and the like. Therefore, the printing paper can be replaced under the condition that the front surface of the all-in-one machine faces upwards by hinging the turnover plate on the cover surface.

Further, since the turnover plate is required to be lifted when the printing paper is replaced and the printing paper should be compacted when the turnover plate falls down, a stop rod is provided at the bottom of the turnover plate, and the stop rod is provided in a direction parallel to the paper outlet; and a locking unit is provided between the turnover plate and the cover surface to guarantee that the turnover plate cannot be turned up freely during normal work of the all-in-one machine and printing by the printing mechanism.

In the embodiment, the locking unit completes a locking operation by cooperation of the ratchet wheel and the pawl; the ratchet wheel which can be clamped into the groove of the cover surface is provided at one end of the stop rod, and then the pawl at one end of the turnover plate is pressed down, clamped into the ratchet wheel to limit the ratchet wheel; and when the printing paper needs to be replaced, the pawl is separated from the ratchet wheel.

In addition, the locking unit can also be a self-locking mechanism such as a push-type rebounder, and a person skilled in the art would be able to set it by himself according to requirements, if only it is guaranteed that the printing unit can work normally and the handheld shell is integrated.

Specifically, the touch display screen can be a capacitive touch display screen, and performs a man-machine interaction operation by connection with a control circuit. The fluorescent immune reagent card test mechanism can be triggered with one press to start test via the button.

In the embodiment, the SIM card is used for realizing real-time data intercommunication through GPRS or 4G and uploading data to the public security intranet. The information of the SD card used for storing information such as items, batches and standard curves can be acquired from the SD card socket. In addition to wireless communication such as GPRS or 4G, interaction between the all-in-one test machine and the PC can be completed by a data line via a USB interface, or interaction between the stored information and the all-in-one test machine can be completed by the SD card via the SD card socket. The interaction between the all-in-one test machine and the intelligent machine can also be achieved by a Bluetooth card via a Bluetooth card protocol.

Embodiment 2

The embodiment provides a method for utilizing the all-in-one handheld machine for testing drugs in hairs, which comprises the steps of:

S1, after being power-on, inputting a control instruction via the control instruction input unit, and controlling the identity recognition mechanism and the fluorescent immune reagent card test mechanism to start by the control mechanism according to the control instruction;

S2, placing an identity card of a drug-taking suspect on the handheld shell, automatically sensing and reading identity information of the drug-taking suspect from the identify card by the identity recognition mechanism in real time, and transmitting the identity information to the control mechanism;

S3, determining an item to be tested and retrieving a corresponding reagent card, inserting the reagent card with a hair sample collected from the drug-taking suspect into a reagent card socket of the fluorescent immune reagent card test mechanism via the reagent card inlet, selecting via the control instruction input unit a specific test item to be tested, and starting the test by the fluorescent immune reagent card test mechanism after the selection; and S4, automatically operating the fluorescent immune reagent test card mechanism to complete reagent card incubation , detect a fluorescent signal, convert the fluorescent signal into concentration result for the test item, and transmit the concentration result for the test item to the control mechanism.

The method further includes transmitting by the control mechanism the identity information and the concentration result for the test item of the drug-taking suspect as data to a public security intranet in real time via the SIM card or the Bluetooth card of the communication unit; connecting the data into a network base station and uploading the same to a data center platform by the network base station; and issuing the data by the data center platform via the public security intranet to each monitoring point at which a dynamic monitoring on the drug-taking suspect is realized.

The method further includes controlling by the control mechanism a printing mechanism to print the identity information and the concentration result for the test item of the drug-taking suspect. Specifically, the control mechanism controls the starting of the printing module, the printing module prints the content on the winding-off printing paper to output the printing paper from the paper outlet. The identity information includes the name, the identity card number and the like of the drug-taking suspect, and the concentration result for the test item have the types of drugs and the drug content.

Further, the control mechanism can also interact with the PC via the USB interface and the data line, to display the identity information and the concentration results for the test item of the drug-taking suspect on the PC in real time.

Further, the control mechanism can also store via the SD card socket the identity information and the concentration result data for the test item of the drug-taking suspect in the SD card.

The all-in-one test machine of the invention is a rapid drug detector based on quantum dot fluorescence technology, which can be matched with different test reagent cards to test different types of drugs; the tested materials can be hair, but they can also be blood, urine, saliva and the like; and the all-in-one test machine can be used for testing drug molecules in different types of tested materials; the whole process of test operation is not more than 5 minutes, and especially for the ketamine, the test time is only 2 minutes, which provides powerful support for on-site rapid screening; the fluorescence signal is long-acting and stable, guaranteeing the validity of reading for 1-3 minutes, and the performance of the test instrument is stable without errors after being performed more than ten thousand times.

For those skilled in the art, various corresponding changes and modifications can be made according to the above technical solutions and concepts, and all these changes and modifications should be included in the protection scope of the claims of the present invention.

What is claimed is:

1. An all-in-one handheld machine for testing drugs in hairs, comprising:
   a handheld shell, wherein a control mechanism, a fluorescent immune reagent card test mechanism, an identity recognition mechanism, a control instruction input unit and a power supply module are provided in the handheld shell;
   a surface of the handheld shell is provided with a reagent card inlet that corresponds to a reagent card socket of the fluorescent immune reagent card test mechanism;
   wherein the control mechanism is controllably connected to the fluorescent immune reagent card test mechanism, the identity recognition mechanism and the control instruction input unit, respectively;
   and further wherein the control mechanism, the fluorescent immune reagent card test mechanism, the identity recognition mechanism and the control instruction input unit are all electrically connected to the power supply module;
   and even further wherein the control mechanism is communicatively connected with a communication unit comprising a wireless communication module.

2. The all-in-one handheld machine for testing drugs in hairs according to claim 1, wherein the identity recognition mechanism comprises an identity card reading unit, and the control mechanism is controllably connected to the identity card reading unit.

3. The all-in-one handheld machine for testing drugs in hairs according to claim 2, wherein a card reading area is provided at a position, corresponding to the identity card reading unit, on the surface of the handheld shell.

4. The all-in-one handheld machine for testing drugs in hairs according to claim 1, wherein the all-in-one handheld machine for testing drugs in hairs further comprises a printing mechanism, and further wherein the control mechanism is controllably connected to the printing mechanism, and the printing mechanism is electrically connected to the power supply module.

5. The all-in-one handheld machine for testing drugs in hairs according to claim 4, wherein the printing mechanism comprises a printing module and a printing paper channel, the control mechanism is controllably connected to the printing module, and the printing module is electrically connected to the power supply module; and a paper outlet for outputting printing papers is provided at a corresponding position of the handheld shell.

6. The all-in-one handheld machine for testing drugs in hairs according to claim 5, wherein a turnover plate is provided at a position, corresponding to the printing paper channel, at a front surface of the handheld shell, one side of the turnover plate is hinged to the front surface of the handheld shell, and a stop rod for pressing paper is provided at a bottom of the turnover plate; and a locking mechanism is provided between the turnover plate and the front surface of the handheld shell.

7. The all-in-one handheld machine for testing drugs in hairs according to claim 6, wherein the locking mechanism comprises a ratchet wheel sleeved at one end of the stop rod, a ratchet wheel groove is provided at a position, corresponding to the ratchet wheel, on the front surface of the handheld shell, a pawl is hinged at one end of the turnover plate, and the ratchet wheel and the pawl correspond in position and are matched with each other.

8. The all-in-one handheld machine for testing drugs in hairs according to claim 1, wherein the control instruction input unit is a touch display screen embedded in the front surface of the handheld shell.

9. A method for utilizing the all-in-one handheld machine for testing drugs in hairs which comprises a handheld shell, wherein a control mechanism, a fluorescent immune reagent card test mechanism, an identity recognition mechanism, a control instruction input unit and a power supply module are provided in the handheld shell; a surface of the handheld shell is provided with a reagent card inlet that corresponds to a reagent card socket of the fluorescent immune reagent card test mechanism; the control mechanism is controllably connected to the fluorescent immune reagent card test mechanism, the identity recognition mechanism and the control instruction input unit, respectively; the control mechanism, the fluorescent immune reagent card test mechanism, the identity recognition mechanism and the control instruction input unit are all electrically connected to the power supply module; and the control mechanism is communicatively connected with a communication unit comprising a wireless communication module, the method comprising the steps of:
   S1, after powering on the handheld machine, inputting a control instruction via the control instruction input unit, and controlling the identity recognition mechanism and the fluorescent immune reagent card test mechanism to start by the control mechanism according to the control instruction;
   S2, placing an identity card of a drug-taking suspect on the handheld shell, automatically sensing and reading identity information of the drug-taking suspect from the identify card by the identity recognition mechanism in real time, and transmitting the identity information to the control mechanism;
   S3, determining an item to be tested and retrieving a corresponding reagent card;
   S4, inserting the reagent card with a hair sample collected from the drug-taking suspect into a reagent card socket of the fluorescent immune reagent card test mechanism via the reagent card inlet;
   S5, selecting via the control instruction input unit a specific test item to be tested, and starting the test by the fluorescent immune reagent card test mechanism after the selection;
   S6, automatically operating the fluorescent immune reagent test card mechanism to complete reagent card incubation, detect a fluorescent signal, convert the fluorescent signal into a concentration result for the test item, and transmit the concentration result for the test item to the control mechanism;
   S7, transmitting by the control mechanism data of the identity information and the concentration result for the test item of the drug-taking suspect as data to a public security intranet in real time via a wireless communication module;
   S8, connecting the data into a network base station and uploading the data to a data center platform by the network base station; and S9, issuing the data by the data center platform via the public security intranet to each monitoring point at which a dynamic monitoring on the drug-taking suspect is realized.

10. The method according to claim 9, further comprising controlling by the control mechanism the printing mechanism to print the identity information and the concentration result for the test item of the drug-taking suspect.

11. The method according to claim 9, wherein the identity recognition mechanism comprises an identity card reading unit, and the control mechanism is controllably connected to the identity card reading unit.

12. The method according to claim 11, further comprising controlling by the control mechanism the printing mechanism to print the identity information and the concentration result for the test item of the drug-taking suspect.

13. The method according to claim 11, wherein a card reading area is provided at a position, corresponding to the identity card reading unit, on the surface of the handheld shell.

14. The method according to claim 13, further comprising controlling by the control mechanism the printing mechanism to print the identity information and the concentration result for the test item of the drug-taking suspect.

15. The method according to claim 9, wherein the all-in-one handheld machine for testing drugs in hairs further comprises a printing mechanism, and further wherein the control mechanism is controllably connected to the printing mechanism, and the printing mechanism is electrically connected to the power supply module.

16. The method according to claim 15, further comprising controlling by the control mechanism the printing mechanism to print the identity information and the concentration result for the test item of the drug-taking suspect.

17. The method according to claim 15, wherein the printing mechanism comprises a printing module and a printing paper channel, the control mechanism is controllably connected to the printing module, and the printing module is electrically connected to the power supply module; and a paper outlet for outputting printing papers is provided at a corresponding position of the handheld shell.

18. The method according to claim 17, wherein a turnover plate is provided at a position, corresponding to the printing paper channel, at a front surface of the handheld shell, one side of the turnover plate is hinged to the front surface of the handheld shell, and a stop rod for pressing paper is provided at a bottom of the turnover plate; and a locking mechanism is provided between the turnover plate and the front surface of the handheld shell.

19. The method according to claim 18, wherein the locking mechanism comprises a ratchet wheel sleeved at one end of the stop rod, a ratchet wheel groove is provided at a position, corresponding to the ratchet wheel, on the front surface of the handheld shell, a pawl is hinged at one end of the turnover plate, and the ratchet wheel and the pawl correspond in position and are matched with each other.

20. The method according to claim 9, wherein the control instruction input unit is a touch display screen embedded in the front surface of the handheld shell.

* * * * *